United States Patent [19]
Naughton et al.

[11] Patent Number: 5,827,729
[45] Date of Patent: Oct. 27, 1998

[54] DIFFUSION GRADIENT BIOREACTOR AND EXTRACORPOREAL LIVER DEVICE USING A THREE-DIMENSIONAL LIVER TISSUE

[75] Inventors: Brian A. Naughton, El Cajon; Craig R. Halberstadt, La Jolla; Benson Sibanda, Oceanside, all of Calif.

[73] Assignee: Advanced Tissue Sciences, La Jolla, Calif.

[21] Appl. No.: 636,591

[22] Filed: Apr. 23, 1996

[51] Int. Cl.$^6$ ............................... B01D 63/00; C12N 5/00
[52] U.S. Cl. ...................... 435/297.2; 435/1.2; 435/289; 435/370; 435/375; 210/500.21
[58] Field of Search ............................. 435/297.2, 289.4, 435/299.1, 375, 395, 1.2, 1.3, 370; 210/500.21

[56] References Cited

U.S. PATENT DOCUMENTS

| | | | |
|---|---|---|---|
| 3,734,851 | 5/1973 | Matsumura | 210/632 |
| 3,997,396 | 12/1976 | Delente | 435/400 |
| 4,107,937 | 8/1978 | Chmiel | 435/1.3 |
| 4,117,881 | 10/1978 | Williams et al. | 435/1.3 |
| 4,200,689 | 4/1980 | Knazek et al. | 435/2 |
| 4,853,324 | 8/1989 | Viles et al. | 435/375 |
| 5,043,260 | 8/1991 | Jauregui | 604/4 |
| 5,081,035 | 1/1992 | Halberstadt et al. | 435/297.4 |
| 5,266,480 | 11/1993 | Naughton et al. | 435/371 |
| 5,270,192 | 12/1993 | Li et al. | 435/174 |
| 5,290,684 | 3/1994 | Kelly | 435/29 |
| 5,510,254 | 4/1996 | Naughton et al. | 435/370 |
| 5,605,835 | 2/1997 | Hu et al. | 435/297.2 |

FOREIGN PATENT DOCUMENTS

| | | |
|---|---|---|
| WO 90/13639 | 11/1990 | WIPO . |
| WO 93/16171 | 8/1993 | WIPO . |
| 96/09876 | 9/1994 | WIPO . |

OTHER PUBLICATIONS

Gunn, 1938, "Hereditary Alcoholic Jaundice," *J. of Heredity* 29:137–139.
Rapoport, 1958, "The Structural and Functional Unit in the Human Liver (Liver Acinus)," *Anat. Rec.* 130:673–689.
Cornelius et al., 1972, "Animal Model of Human Disease," *Am. J. Pathology* 69:369–372.
Jungermann et al., 1982, "The Glucose/Glucose–6–Phosphate Cycle in the Periportal and Perivenous Zone of Rat Liver," *Eur. J. Biochem.* 123:429–436.
Thurman and Kaufmann, 1985, "Sublobular Compartmentation of Pharmacologic Events (SCOPE): Metabolic Fluxes in Periportal and Pericentral Regions of the Liver Lobule," *Hepatology* 5: 144–151.
Haussinger and Gerok, 1986, "Metabolism of Amino Acids and Ammonia," In: *Regulation Of Hepatic Metabolism. Intra–And Intercellular Compartmentation,* Thurman RG, Kaufman FC, Jungermann K, eds., New York, Plenum, 253–291.
Naughton et al., 1987, "Hematopoiesis on Nylon Mesh Templates. I. Long Term Culture of Rat Bone Marrow Cells," *J. Med.* 18:219–250.
Traber et al., 1988, "Physiologic Significance and Regulation of Hepatocellular Heterogeneity," *Gastroenterology* 95:1130–1143.
Naughton et al., 1989, "A Physiological Skin Model for In Vitro Toxicity Studies," 183–189, *Alternative Methods in Toxicology. In Vitro Toxicology: New Directions* vol. 7, (A.M. Goldberg, ed.) Mary Ann Liebert Publishers, New York.
Naughton et al., 1989, "Hematopoiesis on Nylon Mesh Templates," *Ann. NY Acad. Sci.* 554:125–140.
Naughton et al., 1991, "Long Term Liver Cell Cultures as Potential Substrates for Toxicity Assessment," 193–202, *In Vitro Toxicology: Mechanisms and New Technology* (A.M. Goldberg, ed.) Mary Ann Liebert Publishers, New York).
Takahashi et al., 1991, *Digestive Diseases and Sciences* 36(9):1327–1340.
Landeen et al., 1992, "Characterization of Human Dermal Replacement," *Wounds* 4:167–175.
Chowdhury et al., 1993, "Gunn Rat: An Animal Model for Deficiency of Bilirubin Conjugation," *Hepatic Transport and Bile Secretion,* Travolini and Berk, eds., Raven Press, NY, pp. 713–719.
Goresky et al., 1993, "Kinetic Models of Hepatic Transport at the Organ Level", 11–53, In: *Hepatic Transport and Bile Secretion: Physiology and Pathophysiology,* Tavoloni N and Berk PD, eds., Raven Press, NY.
Langer et al., 1993, "Tissue Engineering," *Science* 260:920–926.
Slivka et al., 1993, "Characterization, Barrier Function, and Drug Metabolism of an In Vitro Skin Model," *J. Invest. Dermatol.* 100:40–46.
Halberstadt et al., 1994, "The In Vitro Growth of a Three–Dimensional Human Dermal Replacement Using a Single–Pass Perfusion System," *Biotechnology and Bioengineering* 43:740–746.

*Primary Examiner*—Leon B. Lankford, Jr.
*Assistant Examiner*—Christopher R. Tate
*Attorney, Agent, or Firm*—Pennie & Edmonds LLP

[57] ABSTRACT

A tissue engineering bioreactor is disclosed for growing three-dimensional tissue. Cells are seeded onto a mesh and provided with two media flows, each contacting a different side of the cells. The media flows contain different concentrations of nutrients, allowing nutrients to be delivered to the cells by diffusion gradient. The bioreactor can be used to grow liver tissue, and designed as an extracorporeal liver assist device in which blood or plasma is exposed to the three-dimensional liver tissue. The blood or plasma from a patient directed to flow against the liver tissue. The liver tissue is further exposed on its opposite side to media providing nutrients and gases. The device provides porous boundaries between the blood or plasma, tissue, and media, allowing nutrient and protein delivery by diffusion gradient to dialyze a patient's blood.

22 Claims, 7 Drawing Sheets

DIFFUSION GRADIENT BIOREACTOR AND EXTRACORPOREAL LIVER DEVICE USING A THREE-DIMENSIONAL LIVER TISSUE

FIELD OF THE INVENTION

The present invention relates to methods and apparatuses for culturing three-dimensional mammalian tissue, especially liver tissue. More particularly, the present invention relates to bioreactors capable of growing and sustaining three dimensional tissue cultures comprising multifunctional cells that operate via a diffusional or osmotic pressure gradient on either side of the cultured tissue.

The present invention is suited to the culturing of three-dimensional mammalian tissues for purposes of transplantation or implantation in vivo, in vitro toxicology testing, continuously producing biological cell products such as proteins, delivery of genes to tissue for ex vivo gene therapy, and as the primary component of an extracorporeal organ assist device. In particular, the present invention is suited to the culturing of three-dimensional liver tissue, and the use of liver tissue in a bioreactor as an extracorporeal liver assist device.

BACKGROUND OF THE INVENTION

The past decade has shown great advances in the area of growing tissues and organs in vitro (Langer et al., 1993, "Tissue Engineering," *Science* 260:920–926). One such system for culturing three-dimensional tissues is described in U.S. Pat. No. 5,266,480 to Naughton et al. The culture system of Naughton et al. involves seeding stromal cells from a tissue of interest onto a porous substrate. As the stromal cells grow in this environment, they produce an extracellular matrix and deposit growth factors that contribute to the development of a three-dimensional tissue. This static cell culture milieu provides the necessary microenvironment for cell-cell and cell-matrix communication as well as an adequate diffusional environment for delivery of nutrients and removal of waste products. When the stromal tissue has grown and has developed into a three-dimensional tissue, it is ready for the seeding of the parenchymal cells of interest. The resulting system provides an "in vivo" environment for the full differentiation of the tissue. This system has been used to culture bone marrow tissue (Naughton et al., 1987, "Hematopoiesis on Nylon Mesh Templates. I. Long Term Culture of Rat Bone Marrow Cells," *J. Med.* 18:219–250; Naughton et al., 1989, "Modulation of Long-Term Bone Marrow Culture by Stromal Support Cells," *Ann. NY Acad. Sci.* 554:125–140); skin tissue (Landeen et al., 1992, "Characterization of Human Dermal Replacement," *Wounds* 4:167–175; Naughton et al., 1989, "A Physiological Skin Model for In Vitro Toxicity Studies," 183–189, *Alternative Methods in Toxicology, In Vitro Toxicology: New Directions* Vol. 7, (A. M. Goldberg, ed.) Mary Ann Liebert Publishers, New York; Slivka et al., 1993, "Characterization, Barrier Function, and Drug Metabolism of an In Vitro Skin Model," *J. Invest. Dermatol.* 100:40–46; U.S. Pat. No. 5,266,480); and liver tissue (Naughton et al., 1991, "Long Term Liver Cell Cultures as Potential Substrates for Toxicity Assessment," 193–202, *In Vitro Toxicology: Mechanisms and New Technology* (A. M. Goldberg, ed.) Mary Ann Liebert Publishers, New York).

While many methods and bioreactors have been developed to grow tissue masses for the purposes described above, these bioreactors do not adequately simulate in vitro the mechanisms by which nutrients and gases are delivered to tissue cells in vivo. Cells in living tissue are "polarized" with respect to diffusion gradients. Differential delivery of oxygen and nutrients, as occurs in vivo by means of the capillary system, controls the relative functions of tissue cells and perhaps their maturation as well. Thus, prior art bioreactors that do not simulate these in vivo delivery mechanisms cannot be used to culture a wide variety of three-dimensional tissues.

The tissue culturing system and bioreactors of the present invention improve on the prior art methods of culturing three-dimensional tissues by using diffusion gradients to deliver nutrients to, while simultaneously removing metabolic waste products from, the three-dimensional tissue culture. Such a diffusion-driven delivery mechanism enhances delivery of nutrients and removal of waste products and simulates in vitro the diffusional mechanisms whereby nutrients are delivered to mammalian cells in vitro, thereby optimizing the growth and differentiation of cell cultures grown in vitro. Thus, a wide variety of three-dimensional tissues having multifunctional cells can be cultured and sustained using the present invention.

Currently available bioreactor techniques for growing tissue masses in general include hollow fiber techniques, static maintenance reactor systems, fluidized bed reactors, and flat-bed, single-pass perfusion systems.

The most commonly used bioreactors involve hollow fibers. Hollow fiber reactors generally use numerous hollow fiber membranes of appropriate composition and porosity for the cells being cultured. They are often referred to as artificial capillary systems. (See, for example, U.S. Pat. No. 4,200,689 to Knazek et al.) Culture medium flows through the middle of the hollow fibers, and the cells are located on the outside of the fibers and in the spaces between the fibers. Nutrients flow through the hollow fibers to the cells. This type of bioreactor is not capable of growing thick tissue, as the cells only grow in the small interstitial spaces between the hollow fibers.

Hollow fibers are also disclosed in U.S. Pat. No. 5,081,035 to Halberstadt et al. In this system, cells are also grown in the interstitial spaces of an array of capillary tubes. Convective forces are used to maintain a constant nutrient gradient to all of the cells growing in the interstitial areas of the bioreactor. This method is also limited to growing cells in the small areas between the fibers, and cannot be used for a thick tissue.

Another hollow fiber device is described in U.S. Pat. No. 3,997,396 to Delente. In this system, cells are attached to the interstitial spaces of a hollow fiber bundle. An oxygen carrier is passed through the center of the fibers while the cells are incubated in a nutrient medium. As with the previously described hollow fiber devices, this method does not provide a thick cultured tissue and does not utilize osmotic pressure differentials to deliver nutrients to the cells from the nutrient medium.

Yet another hollow fiber device is described in WO 90/13639 to Tolbert et al. However, this system does not utilize osmotic pressure differentials to deliver nutrients to the cultured tissue mass.

A single-pass perfusion bioreactor system is described in Halberstadt et al., 1994, "The In Vitro Growth of a Three-Dimensional Human Dermal Replacement Using a Single-Pass Perfusion System," *Biotechnology and Bioengineering* 43:740–746. In this system a tissue is cultured on a mesh contained in a teflon bag. Media containing nutrients is pumped through the bag using a peristaltic pump. Nutrients in the media diffuse into the tissue and waste products secreted into the media are carried away. While this system has been used to culture relatively thick skin tissue, the method does not drive the delivery of nutrients by way of a diffusion or osmotic pressure gradient.

Generally, the prior art has not found a way to culture a wide variety of three-dimensional tissues. As discussed above, the prior art bioreactors do not simulate in vivo nutrient delivery mechanism, and therefore these bioreactors cannot be used to culture a wide variety of tissues.

A system to provide hepatic assist to patients awaiting transplants or with limited functioning livers has also long been sought. Unlike the kidney, the function of which is basically only to filter, or unlike the heart, the function of which is purely mechanical, the liver has functions that are complex and involve the removal, chemical conversion, and addition to the blood of a multitude of chemicals, or combinations of these functions. Past methods of providing an artificial liver have failed to provide a device that is as effective as a human liver, and which can be used by patients with a wide range of liver malfunctions. The various methods used in the past are described, for example, in Takahashi et al., September, 1991, *Digestive Diseases and Sciences* 36(9).

One popular method has been charcoal hemoperfusion. This method is used for the treatment of acute hepatic failure. Charcoal is used to remove large molecules of high molecular weight from a patient's blood. However, charcoal hemoperfusion acts only to filter the blood and does not replace other complex liver functions such as the chemical conversion of ammonia to urea or cytochrome P450 activity, which is the main detoxification activity of the liver. In addition, chemical components that would be added to the blood by a healthy liver are not supplied using this method.

Another popular method utilizes microporous membranes to filter plasma from whole blood. Toxins are removed from the separated plasma by multiadsorbents and the purified plasma is reinfused through a microfilter which prevents the passage of fine particles of adsorbent back into the blood. This method, like charcoal perfusion, fails to add chemical components to blood that would be supplied by a healthy liver.

An additional method attempted has been the extracorporeal perfusion of a mammalian liver. While theoretically this method can perform the plethora of complex functions of a healthy liver, the method is difficult to perform and relies on donor organs which are difficult to obtain.

Other therapeutic modalities in use include plasma exchange, a hybrid artificial liver and variations thereof. In the plasma exchange method, the plasma of the patient is exchanged for fresh-frozen plasma. This method presents the danger of removing some indispensable substance from the patient's blood, and requires large amounts of normal plasma, which can be expensive and is not a permanent solution to liver failure.

For a hybrid artificial liver, mammalian liver cells are used to perform the functions of the liver that conventional synthetic systems are incapable of performing, probably due to the lack of a complete understanding of the functions of the liver. Various types of liver cells have been used including liver slices or pieces, liver clusters, and isolated hepatocytes. Experiments with this method have been hampered by the fact that the hepatocytes lose metabolic activity in culture over a short period of time.

Other prior art artificial livers have typically used a cultured monolayer of hepatocytes seeded onto a membrane. One such method is described in U.S. Pat. No. 3,734,851 to Matsuma. Briefly, a stream of blood from a living animal is flowed over a semi-permeable membrane that is in contact with a confluent mono-layer of liver cells. A dialysate is flowed over another semi-permeable membrane that is adjacent to the first semi-permeable membrane and which is also in contact with the confluent mono layer of cells. Waste products carried by the blood pass through the first membrane, are acted upon by the cell layer, pass out through the second membrane and are taken up by the dialysate liquid and carried away. At the same time, desirable metabolic products are taken up by the blood stream. Although these methods have also been used with slices of liver tissue, the tissue layers used have been limited to thickness of between 20–100 $\mu$m, (U.S. Pat. No. 3,734,851 to Matsuma), which severely limits the capacity of blood that can be cleansed using this method.

Some other prior art liver assist devices have used artificial capillaries comprising small tubes made of a semi-permeable membrane. Liver cells are seeded on the outside of the tubes, and the medium flows through the capillary-like tubes, which have thin walls (100 $\mu$m). Collagen is most often used to aid in attachment of hepatocytes to the tubes. Again, these devices are limited in the amount of blood that can be efficiently cleansed due to the lack of liver cells available to act on the blood.

Hollow fibers are used in a perfusion device described in U.S. Pat. No. 5,043,260 to Jauregul, in which a porous membrane separates a perfusion compartment from a hepatocyte compartment. The membrane is provided by hollow fibers communicating with perfusion inlets and outlets of the device, with the hepatocytes attached to the outer surface of the fibers. There is also a second set of hollow fibers communicating with a waste inlet and waste outlet.

In PCT application WO 93/16171 to Barker et al., glass beads are utilized as a matrix instead of tubes or a membrane to entrap hepatocytes and allow perfusion.

In general, however, the prior art has not found a way to make the hepatocytes proliferate adequately for a sustainable amount of cells or to form cell-cell interactions similar to liver in vivo. It is believed that one problem with prior art systems is the lack of ability to sustain the multifunctional cells of the liver, whose various functions are dictated at least in part by the cellular architecture of the tissue mass and the relative spacial relationship to the nutrient supply. Accordingly, none of the disclosed devices enable the growth of thick tissue that could be used as an effective extracorporeal liver device.

SUMMARY OF THE INVENTION

An object of the present invention is to provide a bioreactor and method that will allow the growth of three-dimensional tissue.

Another object of the invention is to provide a bioreactor and method for growing and sustaining three-dimensional tissue cultures including multifunctional cells.

It is a further object of the invention to grow and sustain three-dimensional liver tissue in a bioreactor.

It is a further object of the invention to provide an extracorporeal liver assist device which utilizes three-dimensional liver tissue that is cultured within the device itself or a separate bioreactor.

The foregoing and other objects are achieved by this invention which provides a system for maintaining and culturing three-dimensional tissues in vitro. In accordance with an illustrative embodiment of the invention, the system is provided with a bioreactor that has a tissue disposed between two media flows. The tissue is cultured on a porous substrate. A first media flow having a first concentration of solutes is in direct contact with one side of the tissue, and a second media flow having a second concentration of solutes is in direct contact with the opposing side of the tissue. The first concentration of solutes is different than the second concentration of solutes, creating a diffusional or osmotic pressure gradient which causes movement of solutes, including nutrients, through the tissue. The media flows may also be used to supply gases and growth factors to the cells in varying concentrations, depending on the needs of the particular tissue being cultured. Metabolic waste products, including carbon dioxide, are secreted into the media flows and carried away.

In an alternative embodiment, a semi-permeable membrane can be disposed intermediate the tissue and each of the two media flows. A membrane that allows the passage of desired solutes and waste products should be utilized.

In accordance with another illustrative embodiment of the invention, the system is provided with a bioreactor that has a tissue, cultured on a porous membrane, disposed within a housing, with a first space between the tissue and a top portion of the housing, a second space between the opposing side of the tissue and a bottom portion of the housing, media inlet ports for providing a first media flow into the first space and a second media flow into the second space, and at least one media outlet port. As described above, the concentrations of solutes, including nutrients, growth factors and gases, may be different for the first and second media flows such that the solutes, nutrients, growth factors and/or gases move through the tissue by a diffusion or osmotic pressure gradient.

In accordance with yet another illustrative embodiment of the invention, the system is provided with a bioreactor having a tissue, cultured on a porous membrane, located around the inner circumference of a cylindrical housing, with a first space between the tissue and cylindrical housing, a second center space within the cylindrical housing bounded by the opposing side of the tissue, media inlet ports for providing a first media flow to the first space and a second media flow to the second space, and at least one media outlet port. The first and second media flows may have different concentrations of solutes, including nutrients, growth factors and gases, as described above.

In use, the method of growing a tissue involves seeding structural support cells and parenchymal cells on a porous substrate such as a mesh to form a co-culture that will generate a tissue in vitro. The mesh is preferably made of nylon or a biodegradable material and is disposed in a preferably sterile container having openings at each end for media flows. A first media flow, with predetermined levels of concentration of solutes such as various nutrients, gases, and growth factors, flows in direct contact with the cells on one side of the mesh portion. A second media flow, with different levels of concentration of typically different solutes such as nutrients, gases, and growth factors flows in direct contact with the opposing side of said mesh portion. The differing concentrations of solutes in each of the media flows creates a diffusion or osmotic pressure gradient that drives diffusion of the various requirements for cell growth through the tissue stratum. Simultaneously, metabolic waste products diffuse into the media stream, and are carried away.

In another mode of use, one medium stream can be pressurized to produce hydrostatic pressure differences to counteract the osmotic pressure and to provide further control for nutrient delivery.

The present invention offers advantages over previous tissue culturing systems in that nutrient delivery is directed inward from two opposing planes, permitting the creation of, and maintaining the viability of, a thicker tissue substratum. Thus, the diffusion gradient bioreactor of the invention simulates in vitro the mechanisms by which nutrients are delivered to, and waste products are removed from tissues in vivo, allowing for a wide variety of three-dimensional tissues to be cultured.

The bioreactor and resulting cultures have a variety of applications ranging from in vivo transplantation or implantation of tissues grown in the bioreactor, the continuous production of biological materials in vitro, and as an extracorporeal organ assist device for patients suffering from organ failure. In addition, tissue growth in the reactor can be used for in vitro toxicology testing either after removal to a static environment or as assessed by other means such as the metabolism of drugs or the release of key proteins into the effluent stream from the diffusion gradient bioreactor system.

The bioreactor can be used to grow three-dimensional tissues for the production of a wide variety of biological materials and drugs, including but not limited to, monoclonal antibodies, viral vaccines, hormones, lymphokines, enzymes, tumor-specific antigens, and viral insecticides. To grow a tissue, structural support cells are seeded onto the mesh and provided with media flows to deliver the required nutrients and simultaneously remove waste products produced by the cells. Once the structural support cells have become established, such as, for example, when the structural support cells have grown to confluence, tissue-specific or parenchymal cells are added to the mesh. The content of one or both of the media flows may be altered at this point to meet the needs of the tissue-specific cells.

Once the cells have grown into a three-dimensional tissue, the media flow may be stopped and the tissue can be used or preserved for future use. To preserve the tissue, cryopreservative is added, and the tissue is frozen, preferably in the same container that held the tissue in the bioreactor. The tissue can be later defrosted and used as a bioreactor to produce biological materials.

To use the tissue, a first media flow having predetermined concentrations of solutes such as nutrients, growth factors and gases flows in direct contact with one side of the tissue. A second media flow having different concentrations of solutes flows in direct contact with the opposing side of the tissue. Mass transfer within the bioreactor is achieved via a diffusion gradient. The concentrations of solutes and nutrients provided are sufficient to allow the three-dimensional tissue to produce the desired biological product. The product is withdrawn from the bioreactor via the first or second media flow, or both media flows.

The bioreactor can also be used to grow three-dimensional liver tissue, which can further be used as an extracorporeal liver assist device. Liver tissue is grown as described above, using a co-culture of hepatic stromal and hepatocyte cells. Alternatively, liver tissue is grown using a co-culture of hepatic stromal and acidophilic cells.

The three-dimensional tissue can be used or cryopreserved for future use as described above. The tissue can be later defrosted and used as an extracorporeal liver device. To use the tissue, blood is withdrawn from a patient with a malfunctioning liver. The plasma can be separated from the blood if desired. The blood or plasma is then passed through the container with the liver tissue contacting one side of the tissue, while a media flow passes by the opposing side of the tissue. The tissue will act as a functioning liver on the blood or plasma, which can then be returned to the patient.

DETAILED DESCRIPTION OF THE PREFERRED EMBODIMENTS

Figure 1:
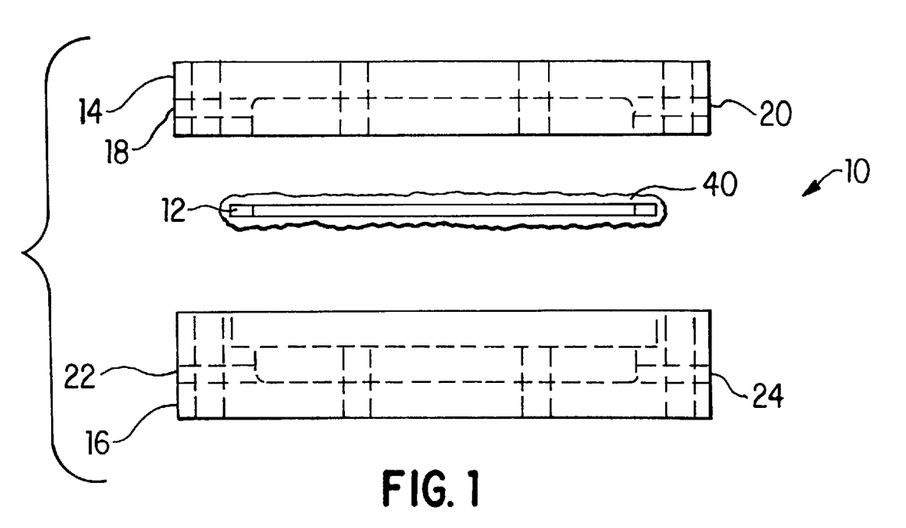
FIG. 1 is an exploded side view of a bioreactor according to the invention.

As shown in FIG. 1, one embodiment of a bioreactor 10 according to the present invention has a tissue 40 which is seeded on a mesh portion 12 in the middle, with a top portion 14 and a bottom portion 16. Tissue in the present usage encompasses mono-layer cell cultures, mono-layer co-cultures of stromal and parenchymal and/or acidophilic cells, three-dimensional tissues having multi-functional cells, as well as all intermediate stages of tissue growth and development achieved during the culturing process.

The top portion 14 and the bottom portion 16 sealingly engage each other. The top and bottom portions each have openings for media flows. The top portion has a first media inlet 18 and first media outlet 20. The bottom portion has a second media inlet 22 and a second media outlet 24. Media supply tubes are provided at the two inlets 18 and 22. Return tubes are provided at the outlets 20 and 24. Media supply tubes may optionally be connected to a peristaltic or other type of pump for delivery of media through the bioreactor.

Top portion 14 and bottom portion 16 can be made of any material suitable for culturing mammalian cells. Preferably, the material can be easily sterilized, such as plastic.

Mesh portion 12 may be of any material and/or shape that allows cells and/or tissue to be attached to it (or can be modified to allow cells and/or tissue to attach to it) and that allows cells and/or tissue to grow in more than one layer into a three-dimensional tissue. A number of different materials can be used to form mesh portion 12, including, but not limited to, Goretex™; nylon (polyamides); dacron (polyesters); polystyrene; polypropylene; polyacrylates; polyvinyl compounds (e.g. polyvinylchloride); polycarbonate (PVC); polytetrafluoroethylene (PTFE); teflon; thermanox (TPX); nitrocellulose; cotton; polyglycolic acid (PGA); cat gut sutures; cellulose; dextran; gelatin, etc. Any of these materials may be woven into a mesh, for example, to form a support for a three-dimensional tissue.

Certain materials, such as nylon, polystyrene, etc. are less effective as substrates for cellular and/or tissue attachment. When these materials are used as the mesh portion it is advisable to pre-treat the mesh prior to inoculation of stromal cells in order to enhance the attachment of stromal cells to the mesh. For example, prior to inoculation with stromal cells, nylon meshes could be treated with 0.1M acetic acid, and incubated in polylysine, FBS, and/or collagen to coat the nylon. Polystyrene could be similarly treated using sulfuric acid.

Where the three-dimensional tissue is itself to be implanted in vivo, it may be preferable to use biodegradable meshes such as polyglycolic acid, catgut suture material, collagen, polylactic acid or hyaluronic acid. Where the tissues are to be maintained for long periods of time or cryo-preserved, non-degradable materials such as nylon, dacron, polystyrene, polyacrylates, polyvinyls, teflons, cotton, etc. may be preferred. A convenient nylon mesh which could be used in accordance with the invention is Nitex, a nylon filtration mesh having an average pore size of 210 µm and an average nylon fiber diameter of 90 µm (#3-210/36, Tetko, Inc., NY).

After a tissue has been grown in the bioreactor, it can be frozen and preserved in the bioreactor container itself. Cryopreservative is added through the media inlet ports, and then the inlet and outlet ports are sealed, providing a closed environment. The tissue can then be frozen in the container, and defrosted when needed.

Methods for cryopreserving tissue will depend on the type of tissue to be preserved and are well known in the art. For example, methods for freezing bone marrow and biological substances in accordance with a precalculated temperature and time curve are disclosed in U.S. Pat. Nos. 4,107,937 and 4,117,881.

The tissues and bioreactors of the invention can be used in a wide variety of applications. These include, but are not limited to, transplantation or implantation of the cultured tissue in vivo; screening cytotoxic compounds, allergens, growth/regulatory factors, pharmaceutical compounds, etc. in vitro; elucidating the mechanisms of certain diseases; studying the mechanisms by which drugs and/or growth factors operate; diagnosing and monitoring cancer in a patient; gene therapy; the production of biological products; and as the main physiological component of an extracorporeal organ assist device, to name a few. These and other applications are well-known in the art, and are described, for example, in U.S. Pat. No. 5,266,480 to Naughton et al. The tissues cultured by means of the bioreactors of the invention are particularly suited for the above applications, as the bioreactors allow the culturing of three-dimensional tissues having multifunctional cells. Thus, these tissues effectively simulate tissues grown in vivo.

In one embodiment of the invention, the bioreactors of the invention could be used in vitro to produce biological cell products in high yield. For example, a cell which naturally produces large quantities of a particular biological product (e.g. a growth factor, regulatory factor, peptide hormone, antibody, etc.) or a host cell genetically engineered to produce a foreign gene product, could be cultured using the bioreactors of the invention in vitro. Once the tissue has grown to a thickness of about 100 μm, preferably at least about 1 mm, the tissue disposed in the bioreactor can be used to produce the biological product in high yield.

To use the bioreactor to produce biological products, a first media flow having a first concentration of solutes such as nutrients, growth factors and gases flows in through port 18 and out through port 20, over one surface of a tissue 40 seeded onto mesh 12. A second media flow having a second concentration of solutes flows in through port 22 and out through port 24, in direct contact with the opposing side of the tissue. The concentrations of solutes and nutrients provided are such that the tissue layer produces the desired biological product. Product is then excreted into the media flows, and can be collected from the effluent stream using techniques that are well-known in the art.

Figure 2:
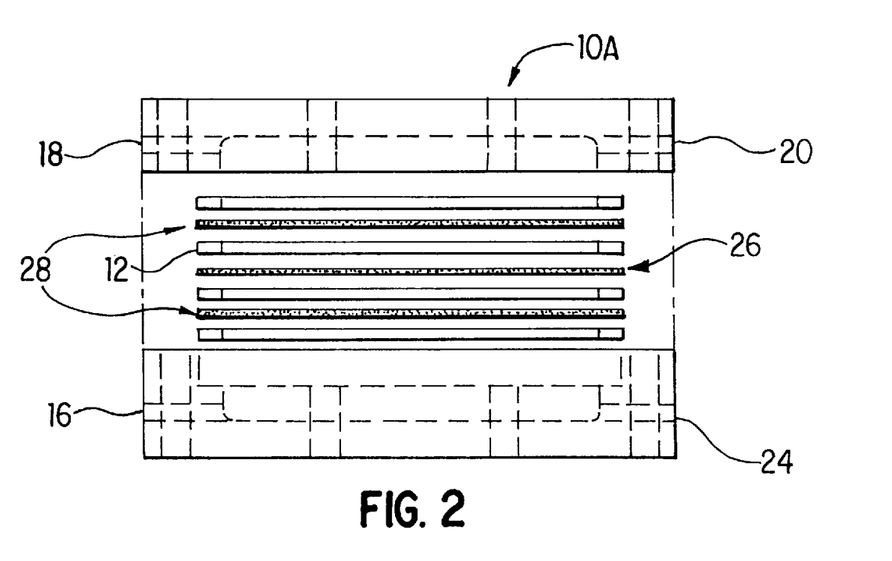
FIG. 2 is an alternative embodiment of a bioreactor according to the invention including membranes.
Figure 3:
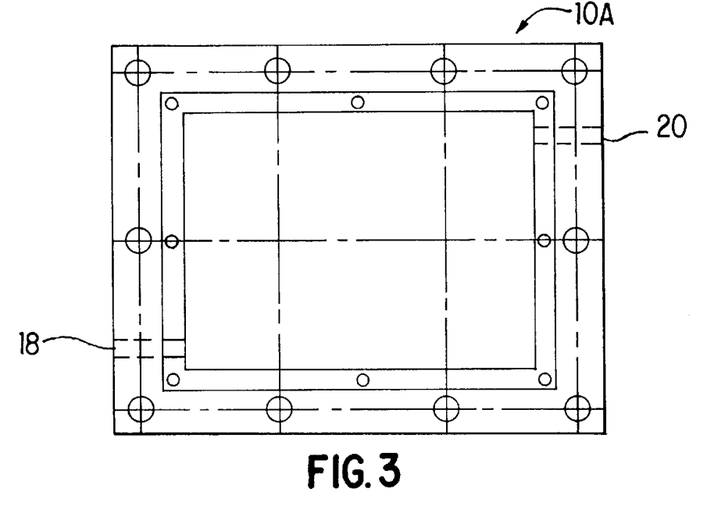
FIG. 3 is a top view of the bioreactor shown in FIGS. 1 and 2.

FIGS. 2 and 3 illustrate an alternative embodiment of the present invention wherein bioreactor 10A has a tissue (not shown) seeded onto mesh portion 12. Mesh portion 12 is disposed between two semi-permeable membranes 28. As illustrated in FIG. 2, a blank mesh 26 (mesh that does not have a tissue seeded onto it) may be used to separate two or more tissues. As with bioreactor 10, ports are provided for appropriate media flows.

The pore size cut-off ranges of semi-permeable membranes 28 will depend on the type of tissue being cultured and the nutrients, growth factors, etc. necessary to maintain the tissue. For growth of liver tissue, the membranes used should have a pore size cut-off of about 200,000 to 400,000 Dalton, preferably about 400,000 Dalton, but in any case the membranes used should allow diffusional egress of culture products and inflow of the nutrients and gases used to culture the tissue. The pores should also be of a size sufficient to prevent cells from crossing through the membrane.

When used as an extracorporeal liver assist device, the pore size cut-off ranges of membranes 28 should be small enough to exclude immunoglobulin G (IgG), typically about 90,000 to 140,000 Dalton and preferably about 120,000 Dalton.

When the bioreactor is being used for the continuous production of biological materials, the membranes disposed on each side of the three-dimensional tissue may have different pore size cut-off ranges such that as medium perfuses through the tissue the secreted cell product diffuses into only one of the media flows. The pore size cut-off ranges of the membranes selected will depend, in addition to the nutrients necessary to sustain the tissue, on the size of the desired cell product and will be apparent to those having skill in the art.

Figure 4:
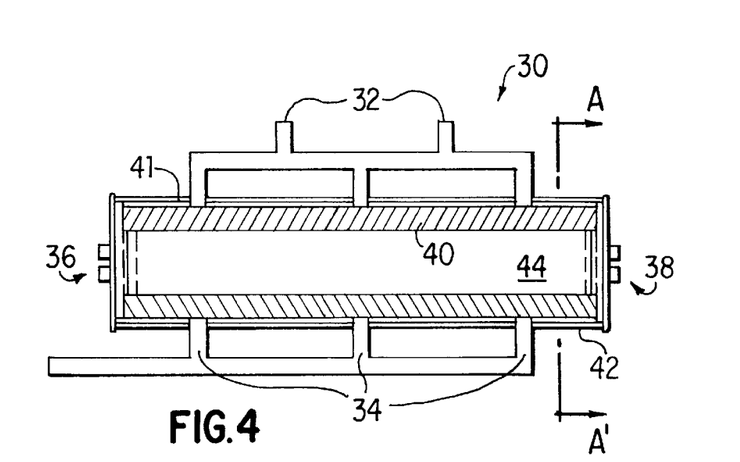
FIG. 4 is a cross-sectional view of an alternative embodiment of a bioreactor, which may also serve as an extracorporeal liver device.
Figure 5:
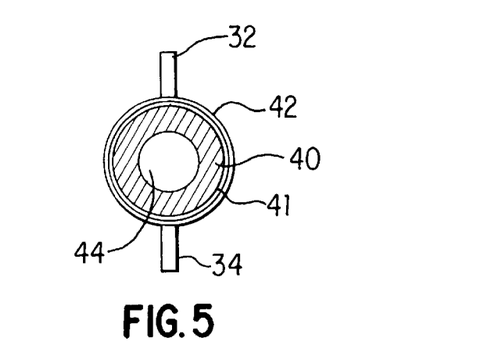
FIG. 5 is a cross-section of the device of FIG. 4 through line A—A'.

FIGS. 4 and 5 illustrate an alternative embodiment of a bioreactor according to the invention, which may be used as an extracorporeal device as well as for growth of tissue. Alternative bioreactor 30 is designed as concentric cylinders. The outermost cylindrical area is bounded by an outer cylinder 42 made of a preferably hard, impermeable material, such as plastic. Tissue 40 is located next to the outer cylinder. Tissue 40 is cultured on a mesh portion (not shown in FIGS. 4 and 5) as described above. Inlet ports 32 feed media that flows in the space 41 between tissue 40 and outer cylinder 42. The media leaves through outlet ports 34. Additional inlet ports 36 are provided that flow into central area 44 of the bioreactor, and exit through outlet ports 38. Central area 44 is exposed to the side of tissue 40 opposing that which contacts space 41.

In an alternative embodiment, the three-dimensional tissue is disposed between two membranes (not shown in FIGS. 4 and 5) as described above.

Figure 6:
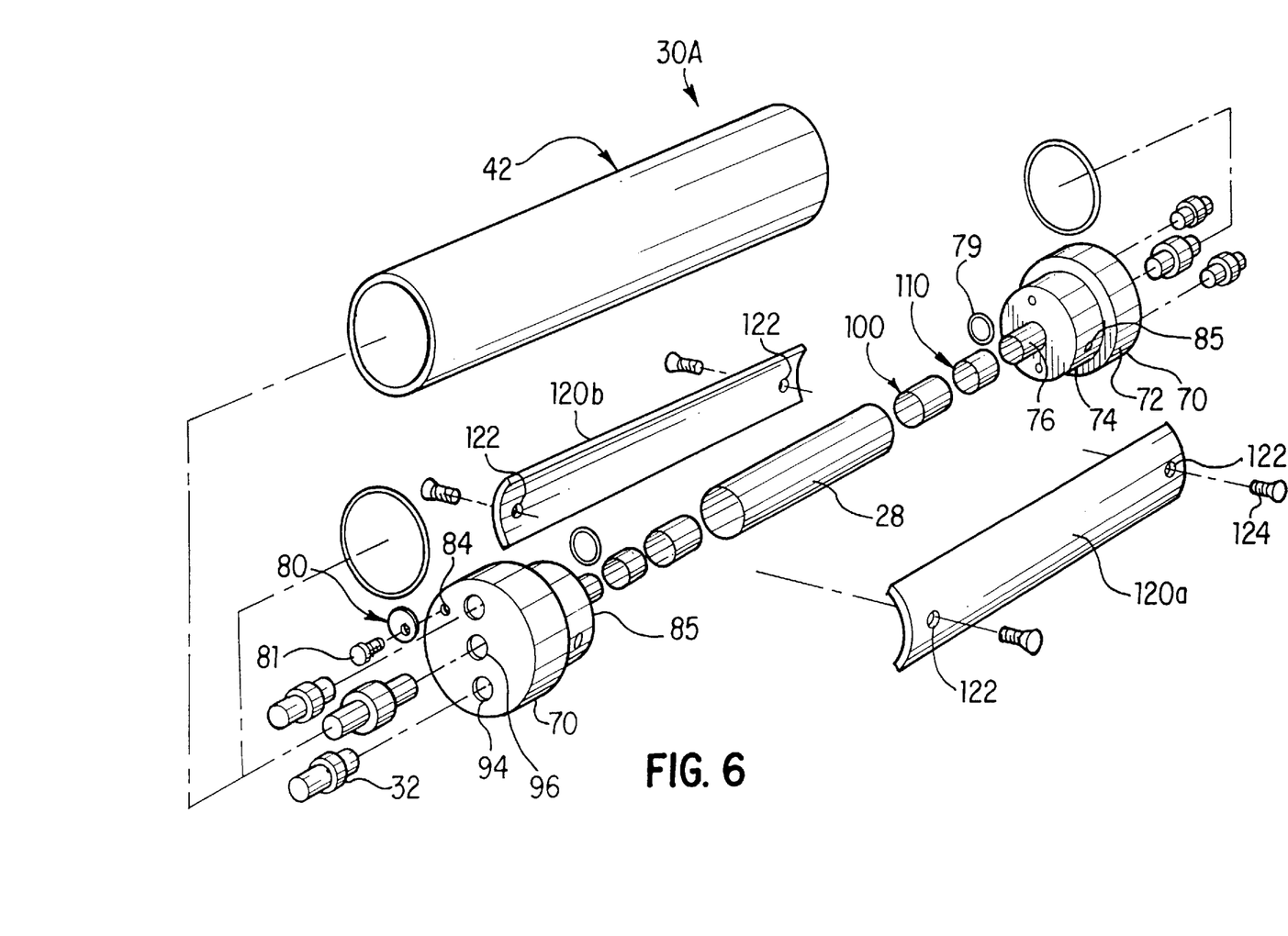
FIG. 6 is an exploded view of a preferred bioreactor, which may also serve as an extracorporeal liver device.
Figures 7, 8:
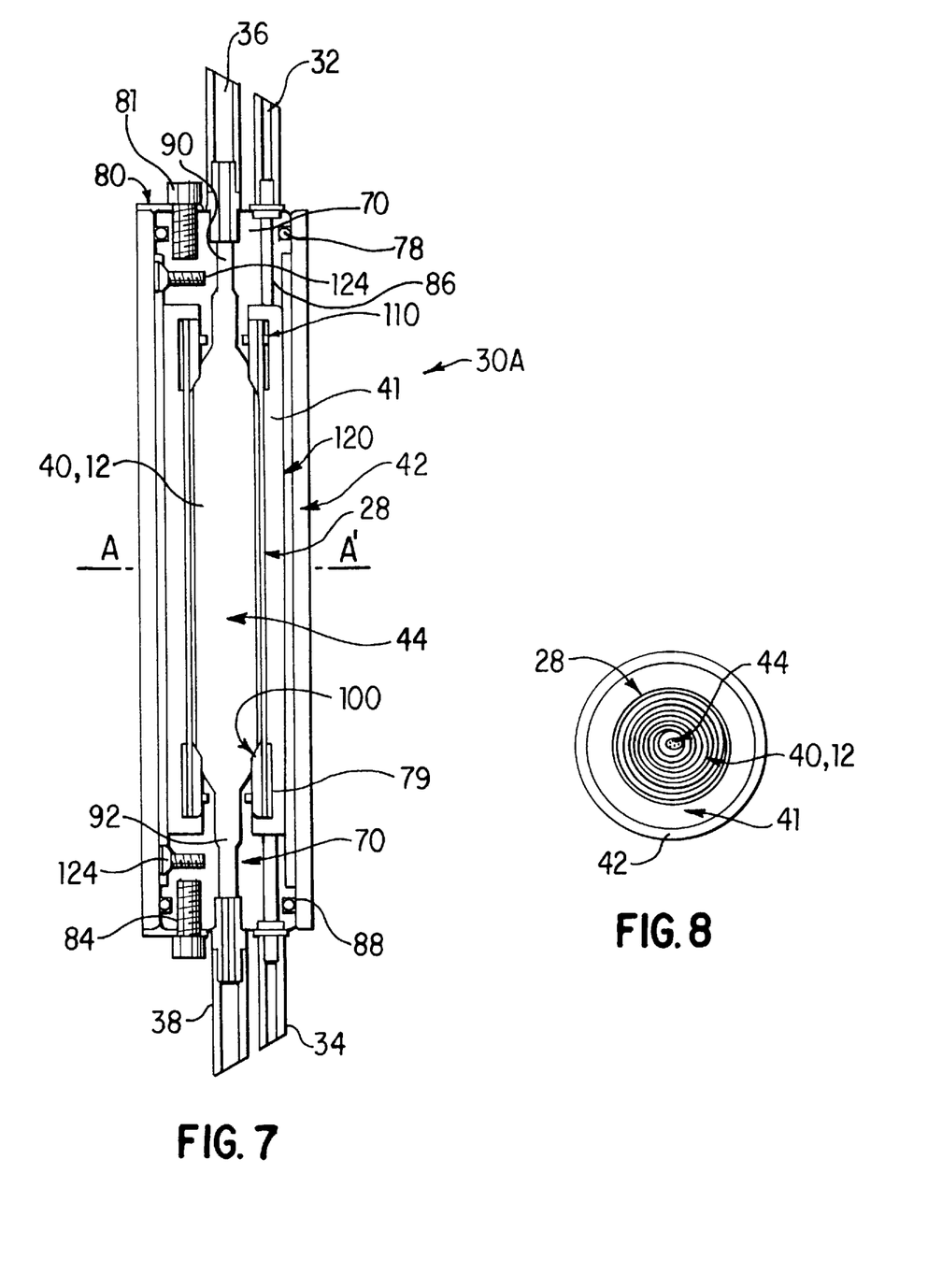
FIG. 7 is a longitudinal cross-section of the device of FIG. 6.
FIG. 8 is a cross-section of the device of FIG. 7 through line A—A' showing a culture on a mesh having an increased surface area.

FIGS. 6 and 7 illustrate a preferred embodiment of a cylindrical bioreactor 30A. The outermost cylindrical area is bounded by an outer cylinder 42 having an inner diameter and an outer diameter, and two end caps 70. The dimensions of outer cylinder 42 will depend on the particular application and/or tissue being cultured. For use as an extracorporeal liver assist device for mice, for example, outer cylinder 42 may have a diameter of about 0.75 to 1 inch and a length of about 6 inches. The dimensions may be easily adapted for a particular application, as will be readily apparent to those having skill in the art.

Outer cylinder 42 can be made from any material that is compatible with the conditions used to culture tissue 40. Preferably, outer cylinder 42 is made of a hard, easily sterilizable material such as polysulfone.

End caps 70 have a first body portion 72 having a first diameter, a second middle body portion 74 having a second diameter smaller than the first diameter, and a third lower body portion 76 having a third diameter smaller than the second diameter. The first diameter of first body portion 72 of end caps 70 sealingly engages outer cylinder 42. Preferably, the first body portion 72 of end cap 70 has a sealing means 78 for providing a tight seal between outer cylinder 42 and end cap 70. Sealing means 78 is preferably an O-ring or annular bead, and more preferably an O-ring. In a particularly preferred embodiment, sealing means 78 is an O-ring composed of Buna-N.

To aid ease of assembly and to properly position outer cylinder 42 over end caps 70, end caps 70 further comprise at least one stopping means 80 affixed to the top of the first body portion 72 of end cap 70. Stopping means 80 extends beyond the outer diameter of outer cylinder 42 when outer cylinder 42 is sealingly engaged with end caps 70. Stopping means 80 is preferably composed of a hard material such as plastic. In a particularly preferred embodiment, stopping means 80 is composed of polysulfone and is affixed to end cap 70 by means of a screw 81 threaded through stopping means 80 into screw hole 84. Screw 81 is preferably composed of nylon.

Referring now to FIG. 7, mesh portion 12, fashioned into a cylinder, is disposed within semi-permeable membrane 28, which has also been fashioned into a cylinder. Tissue 40, seeded onto mesh portion 12 (mesh 12 and tissue 40 are illustrated in FIGS. 7 and 8 as the same element, as tissue 40 is cultured in the interstices of mesh 12), is located around the inner surface of cylindrical membrane 28. Alternatively, in an embodiment not illustrated, mesh portion 12 (and tissue 40) is wrapped around the outer surface of cylindrical membrane 28.

Referring now to FIG. 8, mesh portion 12 (and tissue 40) may be rolled into a cylinder having a plurality of layers to increase the surface area of mesh 12, and concomitantly the surface area of tissue 40 seeded onto mesh 12, and inserted into cylindrical membrane 28.

Referring now to FIG. 7, tissue 40 is disposed within preferred cylindrical bioreactor 30A with the aid of membrane 28, end caps 70, cylindrical insert 100 and cylindrical clamp 110. Cylindrical insert 100 is circumferentially mounted onto the third body portion 76 of end cap 70 so that cylindrical insert 100 sealingly engages end cap 70. In preferred embodiments, the third body portion 76 of end cap 70 has a sealing means 79 for providing a tight seal between cylindrical insert 100 and end cap 70. Sealing means 79 is preferably an O-ring or annular bead, and more preferably an O-ring. In a particularly preferred embodiment, sealing means 79 is an O-ring composed of Buna-N.

Tissue 40, seeded onto mesh 12 is disposed around the inner surface of cylindrical membrane 28, as described above. The length of cylindrical membrane 28 is longer than the length of tissue 40. One end of cylindrical membrane 28 is circumferentially mounted over insert 100. Membrane 28 is sealingly engaged onto insert 100 by means of cylindrical clamp 110, which is circumferentially mounted over membrane 28 and insert 100.

The other end of membrane 28 is affixed to a second end cap 70 as described above.

Additional structural support is provided to preferred cylindrical bioreactor 30A by means of struts 120a and 120b (collectively struts 120). Struts 120 each have a semicircular cross-section as depicted in FIG. 6, and when paired together form a cylinder having an inner diameter approximately equal to the diameter of second body portion 74 of end cap 70, and an outer diameter smaller than the diameter of first body portion 72 of end cap 70. When bioreactor 30A is assembled, struts 120 sealingly engage second body portion 74.

Struts 120 each have two screw holes 122 generally aligned with screw holes 85 of end caps 70 when the bioreactor is assembled. Struts 120 attach to end caps 70 by means of four screws 124, each of which is threaded through a strut screw hole 122 and into an end cap screw hole 85. The screws 124 are preferably made of nylon and are countersunk so as not to obstruct outer cylinder 42.

While the cylindrical strut assembly illustrated in FIG. 6 is preferred for ease of assembly, it is to be understood that a single piece cylinder can also be used as a strut for structural support.

Semi-permeable membrane 28 is disposed within and coaxial with, struts 120, leaving space 41 between the struts and the membrane. Inlet port 32 feeds media that flows through inlet passage 86 and into the space 41 between semi-permeable membrane 28 and struts 120. The media flows through exit passage 88 and exits through outlet 34. Additional inlet port 36 and inlet passage 90 are provided that flow media into center area 44 and out through outlet 38 via outlet passage 92.

Preferably, inlet ports 32 and 36 and outlet ports 34 and 38 comprise tubing fittings or adapters that mate with holes 94 and 96 of end cap 70. The tubing fittings or adapters may mate with holes 94 and 96 by way of a Luer fitting, screw threads or the like. The tubing fittings or adapters may be composed of any material suitable for delivery of nutrients and media for cell culture. Such tubing fittings and adapters are well known in the art of column chromatography, and in particular high performance liquid chromatography (HPLC), and can be found, for example in the products catalogs of Rainin Instrument Co. (Emeryville, Calif.), Pharmacia Biotech Inc. (Uppsala, Sweden) and/or BioRad Laboratories (Richmond, Calif.).

Typically, inlet ports 32 and 36 and outlet ports 34 and 38 comprise tubing fittings or adapters that accept tubing having an inner diameter of about $\frac{1}{32}$ to $\frac{1}{4}$ inch, and more preferably about $\frac{1}{16}$ to $\frac{1}{8}$ inch. In particularly preferred embodiments, inlet port 32 and outlet port 34 comprise tubing fittings or adapters that accept tubing having an inner diameter of about $\frac{1}{8}$ inch, and inlet port 36 and outlet port 38 comprise tubing fittings or adapters that accept tubing having an inner diameter of about $\frac{1}{16}$ inch.

For growth of cells, and in particular liver cells, into a three-dimensional tissue containing multifunctional cells, media containing solutes required for sustaining and enhancing tissue growth is fed into central area 44 through inlet passage 90 via inlet port 36. Solutes in the present usage embodies not only nutrients such as proteins, carbohydrates, lipids, etc., but also oxygen, growth factors and other substances that contribute to cell and/or tissue growth and function.

The media flowing through central area 44 is provided with a different level of solute concentration than the media flowing through outer space 41, creating a diffusion or osmotic pressure gradient of solutes through the tissue that facilitates the development of multifunctional cells.

The functional heterogeneity of tissue parenchymal cells is governed to some extent by their exposure to the nutrients and oxygen present in the afferent blood supply. When nutrients are delivered to tissue via a capillary system, diffusion gradients of nutrients and oxygen form to carry these substances from the blood to the tissue. Similar gradients of carbon dioxide of nitrogenous and other wastes direct these entities to the venous capillary for elimination via the blood.

In the liver, these delivery systems are far more complex because the liver receives substantial amounts of blood from the hepatic artery (rich in oxygen and poor in nutrients) and the hepatic portal vein (rich in nutrients coming from the gut organs and hormones such as insulin but poor in oxygen).

The functional units of the liver have been termed acini (Rapoport, 1958, *Anat. Rec.* 130:637–643). An acinus consists of the terminal branches of a portal venule, a hepatic arteriole, and a bile ductule (Traber et al., 1988, *Gastroenterology* 95:1130–1143). The acinus is bounded by terminal branches of the hepatic vein. To illustrate the functioning of an acinus, cells comprising the acinus can be grouped into three distinct zones (for a figure of an acinus and its respective zones, see Traber et al., 1988, *Gastroenterology* 95:1130–1143). Cells in closest proximity of the terminal branches of the portal venule, hepatic arteriole and bile ductule are defined to be in zone 1. Cells in the vicinity of the terminal hepatic vein are defined to be in zone 3. Cells in between zones 1 and 3 are in zone 2.

As best understood, blood enters the acinus either via a portal venule or a hepatic arteriole. Parenchymal cells in zone 1 are directly exposed to this blood. Some cells in this zone receive arterial blood and some receive venous blood. Blood from both of these sources then flows undirectionally toward the terminal hepatic vein in zone 3. This creates a gradient of oxygen and nutrients from zones 1 to 3.

These gradients drive parenchymal cell metabolism and contribute to the functional heterogeneity of liver cells. For example, cells in zone 1 have a high oxygen uptake, synthesize glycogen from lactate, degrade glycogen to glucose, and form glucose from fats and proteins (gluconeogenesis) whereas cells in the oxygen poor zone 3 display functions related to anaerobic metabolism such as glycolysis and glycogen formation from glucose (Jungermann et al., 1982, *Eur. J. Biochem.* 123:429–436).

If blood flow directions are changed (retrograde perfusion) the functional zones are reversed; hepatocytes in zone 3 display high oxygen utilization whereas those in zone 1 perform glycolysis (Thurman and Kaufmann, 1985, *Hepatology* 5:144–151). Another example of this zonal heterogeneity is in the urea cycle; under normal conditions, ammonia is taken up by hepatocytes in zone 1 and converted to urea. If the liver blood flow is reversed (so that blood is flowed from the terminal hepatic vein into the acinus), ammonia is converted to glutamine instead (Haussinger, 1986, In: *Regulation of Hepatic Metabolism. Intra- And Intercellular Compartmentation,* Thurman R G, Kaufman F C, Jungermann K, eds., New York, Plenum, 253–191).

These findings indicate that the liver microarchitecture is designed for sequential metabolic processes and that this is related to the content and direction of flow of the blood. Normally, the ammonia resulting from protein catabolism enters the liver acinus where it is converted by zone 1 and perhaps zone 2 hepatocytes into urea. The urea then flows "downstream" where hepatocytes in zone 3 convert it to glutamine.

The diffusion gradient bioreactor of the invention is designed to allow for greater control of the microenvironment of cells in a cultured tissue by creating a polarity that mimics in vitro the in vivo conditions. The cultured tissue forms a boundary between two media flows. Differences in glucose concentration and oxygen content, e.g., should establish a polarity in the cultured tissue that is similar to that seen across the liver acinus (i.e., from the hepatic arteriole and portal venule toward the terminal hepatic vein). Likewise, sequential metabolic conversions are possible in the diffusion gradient bioreactor of the invention, but not in other methods of culturing liver cells.

For example, the addition of ammonia to one of the media flows will establish a diffusion gradient whereby ammonia is "directed" through the cultured tissue. If the proper oxygen gradient is also established, parenchymal hepatocytes should convert this ammonia to urea; "downstream" hepatocytes will then transform the urea to glutamine which will diffuse into the media flow on the other side of the tissue. Experiments obtained with a cylindrical bioreactor of the invention used as an extracorporeal liver assist device in rats indicates that this is indeed the case (see Example 7).

Thus, the bioreactors of the invention, by generating a diffusion or osmotic pressure gradient between the two media flows and across a tissue, simulate in vitro the delivery of nutrients, metabolites, regulatory molecules, etc. and removal of waste products that occur in tissues in vivo.

The specific solutes and concentrations thereof in each of the media flows will depend on the type of tissue being cultured and its intended purpose. Generally, growth conditions for culturing specific tissue types in static culture are well-known in the art. (See, for example, U.S. Pat. No. 5,266,480 to Naughton et al. and references cited therein; conditions for culturing liver tissue can be found in U.S. Pat. No. 5,510,254 to Naughton et al.).

The bioreactors of the invention can improve on static growth conditions by providing a diffusion or osmotic pressure gradient across the tissue. Thus, while static culture conditions may be successfully employed in the methods of the present invention, it is specifically contemplated that, due to more closely simulating in vivo environments, diffusion gradient bioreactor cultures may employ lower concentrations of nutrients than are required for static tissue cultures. Generally, the in vivo environment of a particular tissue type can be used as a source of guidance for identifying appropriate solute concentrations and osmotic in each of the media flows.

To determine the proper concentration gradients to culture a particular tissue in vitro, the solute and blood gas concentrations of blood entering and leaving the tissue as well as the perfusion rate of blood through the tissue may be used as a source of guidance. These values may be known, or may be measured using standard art-known techniques. This will give information concerning the metabolic kinetics of the tissue which can then be matched in the culture system. Nutrient utilization and parameters specific to the tissue can be monitored to determine whether proper media solute concentrations have been chosen.

For example, for liver one might wish to measure the synthesis of proteins such as albumin and fibrinogen, look for evidence of an active urea cycle by measuring ammonia disappearance and conversion to urea and/or glutamine, measure cytochrome P450 enzyme-mediated conversion of xenobiotics, etc. Culture conditions can then be adjusted for optimal function. For a detailed analysis of flow modeling to determine the kinetics of hepatic transport, see, Goresky et al., 1993, "Kinetic Models of Hepatic Transport of Organic Solutes", 11–53, In: *Hepatic Transport and Bile Secretion: Physiology and Pathophysiology,* Tavoloni N and Berk P D, eds., Raven Press, NY.

In the case of liver, one medium flow is rich in nutrients and low in oxygen, whereas the other medium flow is relatively nutrient-poor and oxygen rich (see Table 1), simulating the in vivo delivery of nutrients to liver cells.

TABLE 1

NUTRIENT CONCENTRATION GUIDELINES FOR CULTURING LIVER TISSUE

|  | Medium A | Medium B |
|---|---|---|
| amino acids (essential) | * |  |
| buffering salts | = | = |
| choline | = | = |
| dexamethasone or hydrocortisone | = | = |
| fatty acids | * |  |
| glucose | * |  |
| glutamine (supplement) |  | * |
| inositol | = | = |
| iron salts | ** |  |
| minerals (Zn, Se, Cu, Ca, Mg) |  | * |
| oxygen |  | * |
| pancreatic hormones (insulin, | ** |  |
| serum (FBS & ES) † | = | = |
| transferrin (Fe saturated) | = | = |
| vitamins (A, $B_{1,2,12}$, Biotin, C, D, E, folic acid, K) | * |  |

FBS is fetal bovine serum, ES is horse serum
*denotes the medium where the starting solute concentration is higher
**indicates that the solute is present in one of the media but not the other
= indicates equal concentrations of solute in both media
† indicates that serum-free medium may be used; in that instance, bovine serum albumin and factors such as epidermal growth factor, prolactin, somatotropin and other hormones may be added to replace critical serum components.

Diffusion is the major mechanism underlying the bioreactor system of the invention. In addition to establishing two media flows having different concentrations of solutes, one medium flow can be pressurized to produce hydrostatic pressure differences to counteract the osmotic pressure and provide further control for nutrient delivery. Pressure within the bioreactor may be controlled by controlling peristaltic pump rates and hydrostatic pressure. Pressure differentials may also be achieved by varying the position of the bioreactor and/or the media reservoirs. The effects of pressure differentials on diffusion are well defined in the literature.

Typically, minimal differences in total pressure are used at the start of perfusion; the movement of solute molecules through the tissue is governed by osmotic pressure differentials generated by differences in media concentrations of key molecules such as, for example, glucose and oxygen. As the tissue develops in vitro, diffusion may be enhanced by varying flow rates and the hydrostatic pressure of either or both media flows.

The rate at which media is flowed through the bioreactor of the invention may depend on a variety of factors such as the size of the bioreactor, surface area of the tissue, type of tissue and particular application. As discussed above, the media flows on either side of the tissue may have different flow rates. Generally, applicants have found that for culturing liver tissue media flow rates of about 0.5 mL/min. to 1 mL/min. yield good results. Those having skill in the art will be able to adjust the flow rates to suit particular applications.

As will be appreciated by the skilled artisan, one advantage of the invention is that since the cultured tissue is preferably three-dimensional, cells can situate themselves in the tissue stratum in a position that simulates their in vivo environments. Accordingly, a variety of tissues having multi-functional cells can be cultured using the bioreactors of the invention.

Referring now to FIG. 4, once liver cells have developed into a tissue at least about 100 µm, preferably about 1 mm in thickness, the liver tissue disposed in the bioreactor can be used as an extracorporeal liver device. For this use, blood or plasma enters the device through inlet ports 36, and flows next to the liver tissue.

For the extracorporeal liver device, a membrane may be used between the blood or plasma and the liver tissue. If a membrane is used, it should have a pore size cut off in the range to exclude IgG, typically about 90,000 to 140,000 Dalton, and preferably about 120,000 Dalton. The extracorporeal liver device may use whole blood, platelet poor blood, or plasma. Blood or plasma passes through space 44, over one surface of the liver tissue, and an artificial medium containing basic nutrients passes through space 41 over the opposite surface of the tissue from inlet ports 32. Exchange of nutrients and waste products occurs by diffusion as described above.

Figure 9:
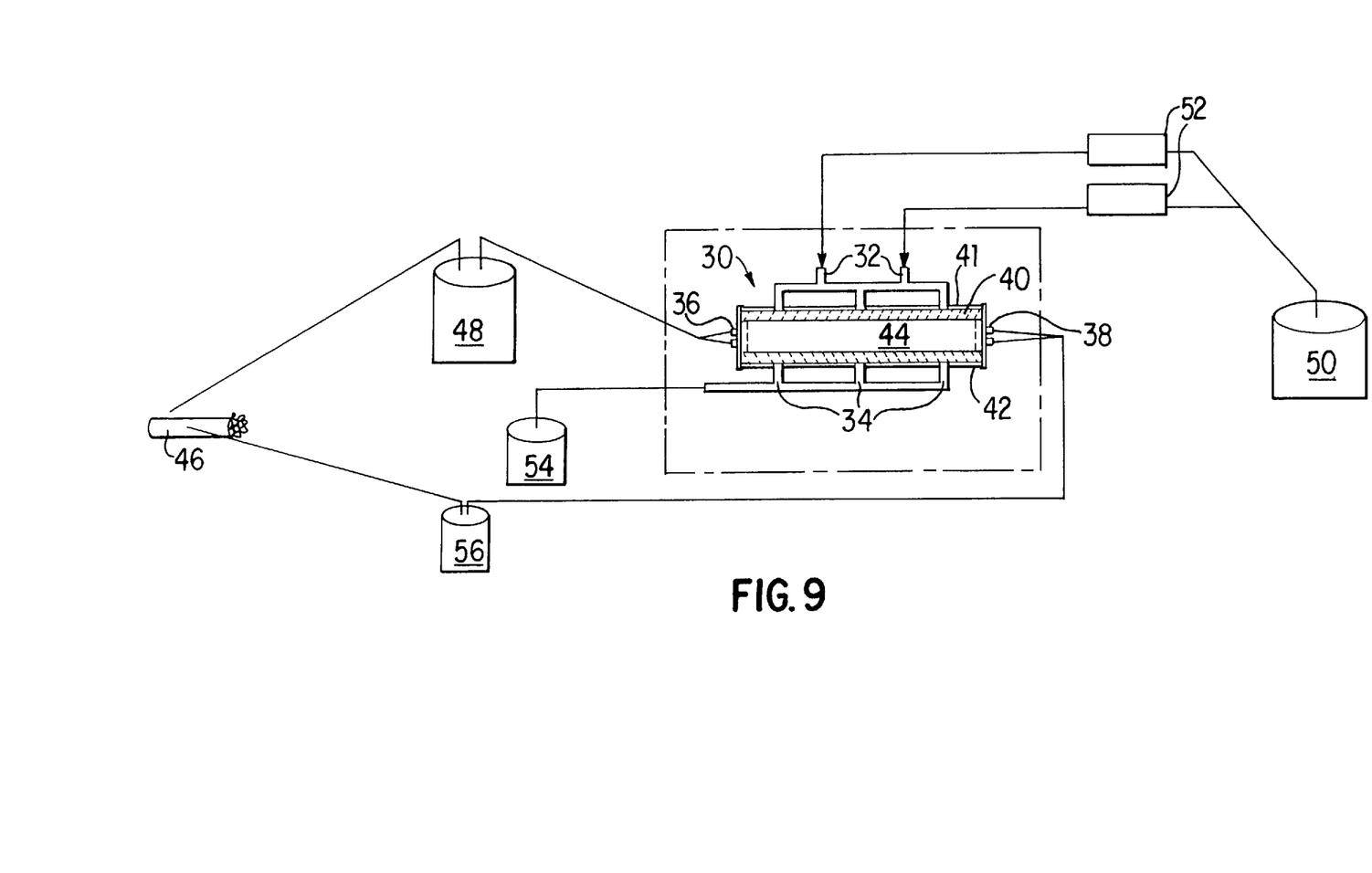
FIG. 9 is a diagram illustrating the use of a bioreactor as an extracorporeal liver device, according to the invention.

The use of the bioreactor as an extracorporeal liver device is diagramed in FIG. 9. Blood is withdrawn from a patient 46. Optionally, the plasma can be separated from the blood cells in a plasmapheresis centrifuge 48. The blood cells are saved for later recombination with the plasma before returning the blood to the patient. The plasma or blood is then fed into the bioreactor 30. To mimic human bodily functions as closely as possible, blood or plasma in need of removal of wastes by a liver flows through the middle of the device 44. Ammonia and other waste products diffuse through the liver tissue 40 due to the diffusion gradient between the media in passages 44 and 41. The liver tissue converts ammonia to urea, which can be removed. Alternatively urea can be removed by the patient's body after the blood is returned to the patient. Any proteins that may be lost from the blood can be added before returning the blood to the patient.

Media is supplied from source 50 and pumps 52. The spent media is drawn into a receiving container 54. When the blood or plasma exits the bioreactor through outlet ports 38, it is recombined with any lost proteins and blood cells if necessary at mixer 56, and returned to the patient 46.

In an alternative embodiment, several bioreactors of the invention may be connected to provide continuous operation for acute or chronic hepatic failure. A plurality of bioreactors 30 of the invention are connected in parallel. A patient's blood is perfused through one bioreactor until the bioreactor can no longer handle the metabolic load. The patient's blood is then diverted to a second bioreactor and the first bioreactor is cleansed to restore its metabolic function. The number of bioreactors used in parallel would be contingent on the recycling time of each bioreactor. For example, few devices would need to be used when the cleansing time is rapid.

The present invention is novel, inter alia, in that its fundamental component is a three-dimensional tissue that is grown in vitro. The three-dimensional tissue may be cultured in the bioreactor of the invention, or it may be cultured elsewhere and inserted into the bioreactor of the invention. In a preferred embodiment, the fundamental component is a three-dimensional liver tissue. The tissue contains not only hepatic parenchymal cells, but also stromal components, which include macrophages, fat storing cells, vascular and biliary endothelial cells, fibroblastic cells, etc. Such multi-functional cells are possible in a single in vitro tissue culture due to the unique diffusion gradient nutrient supply of the present invention. In order to provide all of the functions of a liver and to grow parenchymal cells in vitro, these additional stromal components have been found to be necessary.

The diffusion gradient bioreactor of the invention is suitable for growing virtually any tissue that does not require a liquid-air interface. In addition to liver this would include endocrine and exocrine pancreas, kidney, intestine, blood vessels, bone, cartilage, skin, lung, etc. Also, while the concentric bioreactor as illustrated in FIGS. 4 and 5 is a preferred embodiment, the flat reactors shown in FIGS. 1 and 2 also may be used as an extracorporeal liver assist device.

Various examples demonstrating the use of the invention are provided below. For purposes of illustration only, and not by way of limitation, the bioreactor of the invention is demonstrated by culturing liver tissue and as an extracorporeal liver assist device in Gunn rats. It is to be understood that the bioreactor of the invention can be used to culture a wide variety of tissues, and can be used as an extracorporeal liver, or other organ, assist device in other animals, including humans.

EXAMPLE: Culturing Liver Tissue

A three-dimensional functional liver tissue was cultured in a bioreactor of the invention.

Culturing Conditions

A three-dimensional liver tissue was cultured in a flat bioreactor of the invention generally using the co-culture methods described in U.S. Pat. No. 5,510,254 to Naughton et al. Initial seeding level of parenchymal hepatocytes was $10^8$ cells. Media flow rates were about 0.5 mL/min. The composition of each media flow is provided in Table 2, below.

TABLE 2

NUTRIENT CONCENTRATIONS

| | Medium A (mg/L) | Medium B (mg/L) |
|---|---|---|
| amino acids: | | |
| L-arginine | 200 | 80 |
| L-asparagine | 50 | 25 |
| L-cystine | 65 | 42 |
| L-glutamine | 300 | 80 |
| glycine | 30 | 10 |
| L-histidine | 40 | 15 |
| L-isoleucine | 105 | 50 |
| L-lysine | 140 | 40 |
| L-methionine | 30 | 15 |
| L-phenylalanine | 65 | 15 |
| L-serine | 42 | 26 |
| L-threonine | 90 | 30 |
| L-tryptophan | 16 | 5 |
| L-tyrosine | 70 | 30 |
| L-valine | 95 | 20 |
| buffering salts†: | = | = |
| dexamethasone or hydrocortisone | $10^{-7}$–$10^{-8}$ M | $10^{-7}$–$10^{-8}$ M |
| glucose | 2000 | 500 |
| glutathione | 8 | 3 |
| iron salts: | | |
| Fe(NO$_3$)$_3$ | 0.1 | 0.01 |

TABLE 2-continued

NUTRIENT CONCENTRATIONS

|  | Medium A (mg/L) | Medium B (mg/L) |
|---|---|---|
| $FeSO_4$ | 0.8 | 0 |
| linoleic acid | 20 | 10 |
| minerals: |  |  |
| $CaCl_2$ | 130 | 250 |
| $CuSO_4$ | 0.0001 | 0.0001 |
| Se | 0.0002 | 0.0002 |
| $ZnSO_4$ | 0.0001 | 0.0002 |
| oxygen[††] |  | * |
| pancreatic hormones (insulin) | 0.5 | 0 |
| serum (FBS & ES)[†††] | = | = |
| transferrin (Fe saturated) | 3 | 3 |
| vitamins: |  |  |
| A | 0.1 | 0.1 |
| biotin | 0.2 | 0.1 |
| $B_{12}$ | 0.2 | 0.05 |
| choline | 4 | 3 |
| folic acid | 4 | 2 |
| inositol | 7–20 | 7–20 |
| K | 0.02 | 0.01 |
| niacinamide | 4 | 1 |
| pantothenic acid | 4 | 0.4 |
| pyridoxal | 4 | 2 |
| riboflavin | 0.4 | 0.2 |
| thiamine | 4 | 1 |
| α-tocopherol | 0.1 | 0.1 |

FBS = fetal bovine serum, ES = horse serum
[†]Includes the following hydrated salts. Parentheses indicate a range of concentrations in mg/L. KCl (400), $MgSO_4$ (50–200), NaCl (6000–6400), $NaHCO_3$ (2000–3700), $NaHPO_4$ (140–800).
[††]Medium B will have a differential of + (5–10%)
[†††]Present in approx. equal concentration to 10–15% by volume. Serum-free medium may also be used. In that instance, bovine serum albumin and factors such as epidermal growth factor, prolactin, somatotropin and other hormones may be added to replace critical serum components.
*denotes the medium where the starting solute concentration is higher
= indicates equal concentrations of solute in both media The concentration of albumin and fibrinogen released into the media and the total mean adherent cell count were determined as described in U.S. Pat. No. 5,510,254 to Naughton et al.

Results

Figure 10:
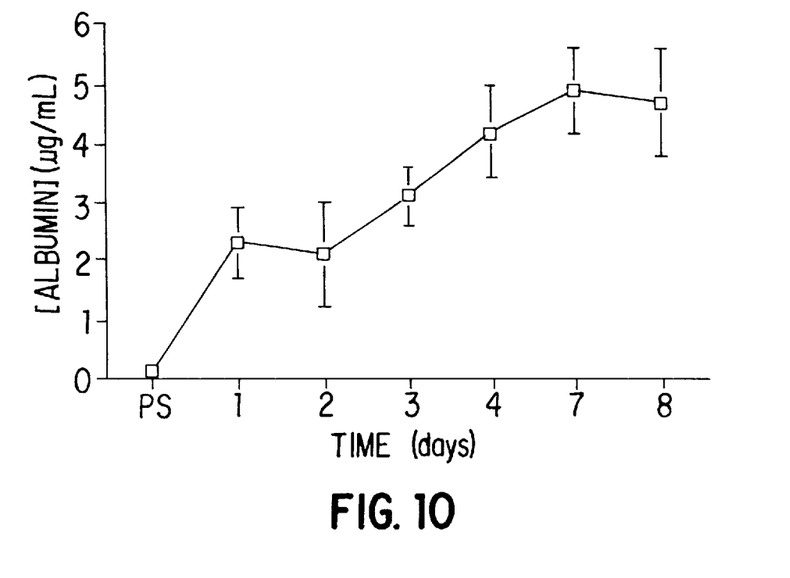
FIG. 10 is a graph illustrating the concentration of albumin released into the medium by liver tissue cultured in a bioreactor of the invention.
Figure 11:
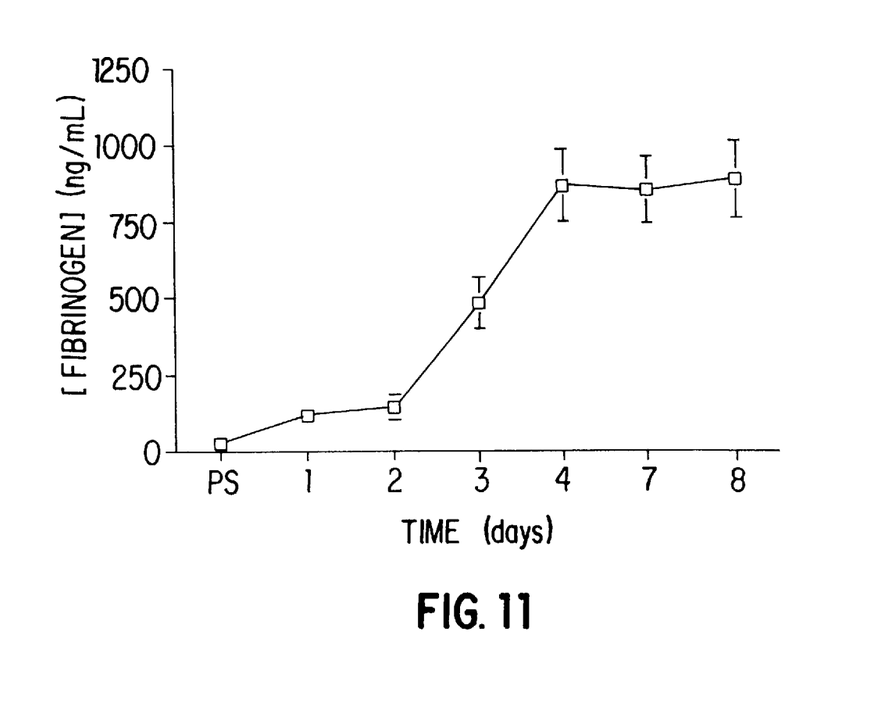
FIG. 11 is a graph illustrating the concentration of fibrinogen released into the medium by liver tissue cultured in a bioreactor of the invention.
Figure 12:
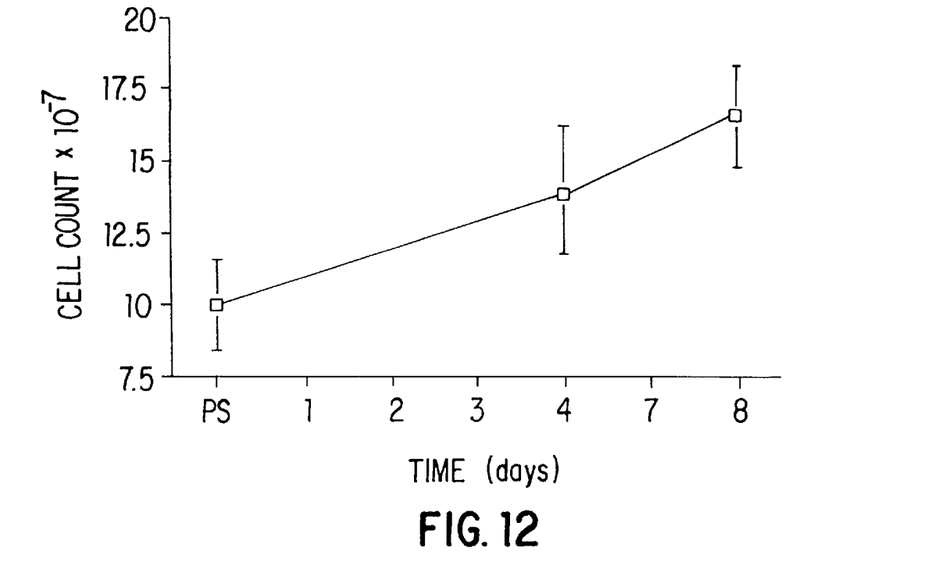
FIG. 12 is a graph illustrating the total adherent mean cell count of a tissue cultured in a bioreactor of the invention.

The tissue cultured in the diffusion gradient bioreactor was much thicker and denser with cells than statically cultured liver tissue. The tissue exhibited active protein synthesis (FIGS. 10 and 11) and also a steady increase in cell number (FIG. 12) over an eight day period. These results demonstrate that the bioreactor of the invention provides a thick, fully functional tissue.

EXAMPLE: Use As An Extracorporeal Liver Assist Device

A bioreactor of the invention was used as an effective extracorporeal liver assist device with Gunn rats.

The Gunn rat model, which is the animal model for Crigler-Naijar syndrome in humans (Cornelius et al., 1938, *Am. J. Pathology* 69:369–372) is an ideal model for demonstrating the efficacy of the bioreactors of the invention as extracorporeal liver assist devices. The Gunn rat has a defect inherited as an autosomal recessive trait in Wistar rats (Gunn, 1938, *J. of Heredity* 29:137–139). The defect, present in homozygous recessive animals, is in the gene encoding UDP-glucuronosyltransferase, an enzyme necessary for the conjugation and biliary excretion of bilirubin (a breakdown product of hemoglobin in senescent red blood cells). The Gunn rat therefore cannot conjugate and excrete bilirubin and becomes hyperbilirubinemic, having serum bilirubin levels of about 5–20 mg/dL, compared with 1 mg/dL in normal rats (Johnson et al., 1959, *AMA Diseases in Children* 99:591–608, "Deficiency of Bilirubin Conjugation in the Gunn Rat," Re: *Hepatic Transport and Bile Secretion*, Travolini and Berk, eds., Raven Press, NY, pp. 713–719 (1993)).

Experimental Protocol

A three-dimension tissue containing a co-culture of heterozygous (phenotypically normal) Gunn rat stromal and hepatocyte cells was cultured on a nylon mesh (3-210/36 Tetko, N.J.) in a flat bioreactor of the invention as described in the previous Example. The thickness of the cultured liver tissue was about 110–130 μm. The rectangular mesh containing the liver tissue was rolled into a multi-layer cylinder (see FIG. 8), inserted into a semipermeable PTFE tube (120,000 Dalton cut-off; diameter about 0.5 inch) and placed in a cylindrical bioreactor of the invention (diameter about 0.75 inch, length about 6 inches). Thus, the net working "thickness" of the liver tissue was about 0.5 inch.

Blood from the femoral artery of a Gunn rat (total average blood volume ca. 10 to 12 mL) was perfused through the periphery of the bioreactor, separated from the liver tissue by the PTFE tube (schematically illustrated in FIG. 10), at a flow rate of about 0.6–0.8 mL/min with the aid of a peristaltic pump. At the same time, Dulbecco's Modified Eagle Medium was flowed through the center portion of the bioreactor containing the rolled-up tissue at a flow rate of about 0.5 mL/min. Blood flowing out of the bioreactor was returned to the Gunn rat.

The levels of unconjugated and conjugated bilirubin in blood exiting the bioreactor were determined over the course of six hours using the Sigma Total and Direct Bilirubin assay system according to the instruction supplied by Sigma (Sigma Procedure #522/553).

Results

Figure 13:
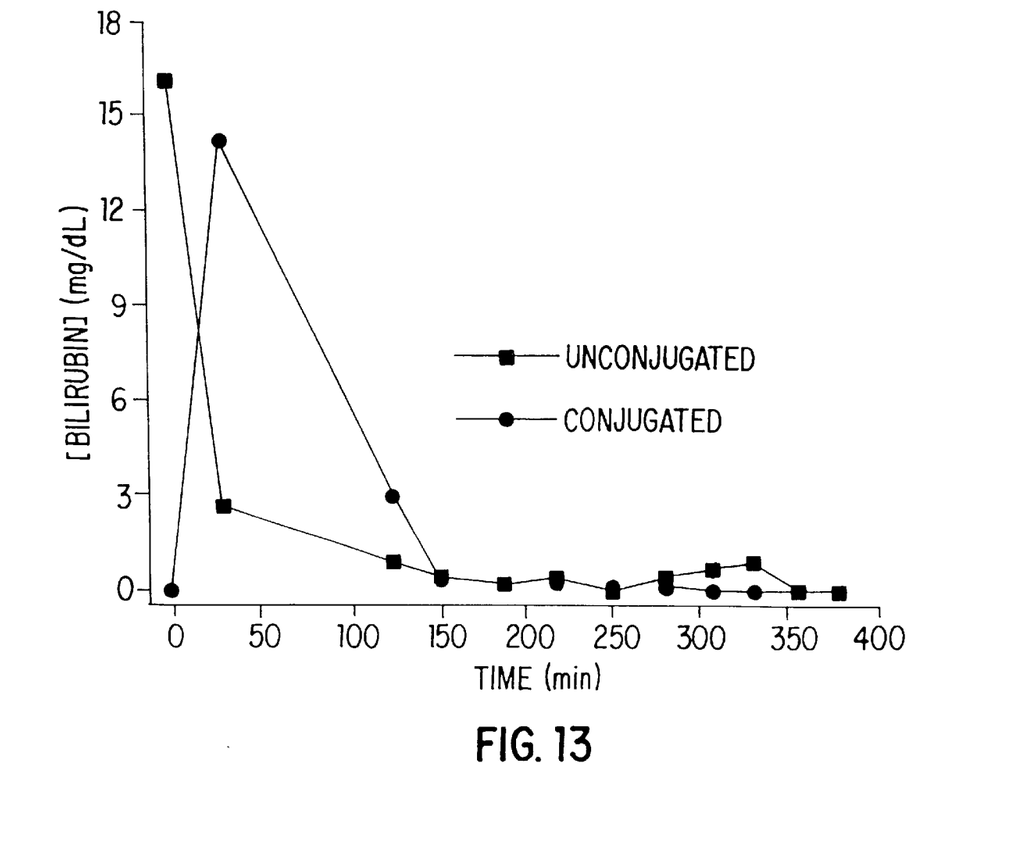
FIG. 13 is a graph showing unconjugated and conjugated bilirubin levels in Gunn rats using a bioreactor of the invention as an extracorporeal liver assist device.

As illustrated in FIG. 13, since the Gunn rat cannot conjugate bilirubin, virtually all of its bilirubin is unconjugated prior to hooking the rat up to the bioreactor (time 0). Approximately 30–35 minutes after hookup to the device, most of the formerly unconjugated bilirubin of the Gunn rat has been conjugated. Over time, the level of this conjugated bilirubin drops as the animal eliminates it via normal metabolic processes; after 2 hours on-line, the levels of plasma bilirubin are barely detectable. These results demonstrate that the cultured tissue is fully functional, and that the diffusion gradient bioreactor of the invention provides an effective extracorporeal liver assist device.

Although the invention has been described in terms of specific embodiments and applications, persons skilled in the art can, in light of this teaching, generate additional embodiments without exceeding the scope or departing from the spirit of the claimed invention. The specific composition of the various elements of the bioreactor system, for example, should not be construed as a limiting factor. Accordingly, it is to be understood that the drawings and descriptions in this disclosure are proffered to facilitate comprehension of the invention and should not be construed to limit the scope thereof.

All references cited in the disclosure are hereby incorporated by reference in their entireties for all purposes.

We claim:

1. A method of dialyzing a patient's blood, the method comprising the steps of:
   (a) providing a bioreactor comprising a housing having a three-dimensional liver tissue with a thickness of at least about 100 μm disposed therein to define separate flow spaces on opposite sides of the liver tissue;
   (b) withdrawing blood from a patient with a malfunctioning liver;
   (c) flowing said blood over one side of said liver tissue;
   (d) flowing nutrient medium over the opposite side of said liver tissue, thereby causing blood waste products to diffuse across said liver tissue; and (e) infusing said blood to the patient.

2. The method of claim 1, wherein said bioreactor is cylindrical.

3. The method of claim 1, wherein said bioreactor further includes a semipermeable membrane disposed intermediate the liver tissue and the flow space through which the blood is flowed.

4. The method of claim 3, wherein the semipermeable membrane has a pore-size cut-off in the range of 90 kD to 140 kD.

5. A method of dialyzing a patient's blood, the method comprising the steps of:

providing a bioreactor comprising a housing having a three-dimensional liver tissue with a thickness of at least about 100 μm disposed therein to define separate flow spaces on opposite sides of the liver tissue;

withdrawing blood from a patient having a malfunctioning liver;

separating said blood into plasma and blood cells and flowing said plasma over one side of said liver tissue;

flowing nutrient medium over the opposite side of said liver tissue, thereby causing waste products in the plasma to diffuse across the liver tissue; and infusing said plasma and blood cells to the patient.

6. The method of claim 5, wherein said bioreactor is cylindrical.

7. The method of claim 5, wherein said bioreactor further includes a semipermeable membrane disposed intermediate the liver tissue and the flow space through which the plasma is flowed.

8. The method of claim 7, wherein the semipermeable membrane has a pore-size cut-off in the range of 90 kD to 140 kD.

9. A method of dialyzing a patient's blood, the method comprising the steps of:

providing a bioreactor comprising a housing having a three-dimensional liver tissue disposed therein, wherein the liver tissue is at least about 100 μm thick and has a first side defining a first flow space and a second side defining a second flow space;

flowing blood from the patient over the first side of the liver tissue;

flowing nutrient medium over the second side of the liver tissue, thereby causing blood waste products to diffuse across the liver tissue; and infusing the blood to the patient.

10. The method of claim 9, wherein said bioreactor housing is a cylindrical housing having an interior and an exterior, the first flow space is disposed between the interior of the cylindrical housing and the first side of the liver tissue and the second flow space is bounded by the second side of the liver tissue.

11. The method of claim 9, wherein said bioreactor further includes a semipermeable membrane disposed intermediate the first side of the liver tissue and the first flow space.

12. The method of claim 11, wherein the semipermeable membrane has a pore-size cut-off in the range of 90 kD to 140 kD.

13. A method of dialyzing a patient's blood, the method comprising the steps of:

(a) providing a bioreactor comprising a housing having a three-dimensional liver tissue with a thickness of at least about 100 μm disposed therein, wherein the liver tissue has a first side defining a first flow space and a second side defining a second flow space;

separating said blood into plasma and blood cells and flowing the plasma over the first side of the liver tissue;

flowing nutrient medium over the second side of the liver tissue, thereby causing blood waste products in the plasma to diffuse across the liver tissue; and infusing the plasma and blood cells to the patient.

14. The method of claim 13, wherein said bioreactor housing is a cylindrical housing having an interior and an exterior, the first flow space is disposed between the interior of the cylindrical housing and the first side of the liver tissue and the second flow space is bounded by the second side of the liver tissue.

15. The method of claim 13, wherein said bioreactor further includes a semipermeable membrane disposed intermediate the first side of the liver tissue and the first flow space.

16. The method of claim 15, wherein the semipermeable membrane has a pore-size cut-off in the range of 90 kD to 140 kD.

17. A method of dialyzing a patient's blood, the method comprising the steps of:

(a) providing a cylindrical bioreactor comprising:

(i) a cylindrical housing having an interior and an exterior; and (ii) a three-dimensional liver tissue having a thickness of at least about 100 μm, said liver tissue having a first side and a second side and being disposed within said cylindrical housing so as to define a first flow space between the first side of the liver tissue and the interior of the cylindrical housing and a second flow space bounded by the second side of the liver tissue:

(b) withdrawing blood from a patient;

(c) flowing blood or plasma from the patient through either the first or the second flow space of the bioreactor;

(d) flowing nutrient medium through the other flow space of the bioreactor; and (e) infusing the blood or plasma to the patient.

18. The method of claim 17, wherein the bioreactor further includes:

(iii) a first inlet port in communication with the first flow space;

(iv) a first outlet port in communication with the first flow space;

(v) a second inlet port in communication with the second flow space; and (vi) a second outlet port in communication with the second flow space.

19. The method of claim 17, wherein said bioreactor further includes a semipermeable membrane disposed intermediate the first side of the liver tissue and the first flow space.

20. The method of claim 19, wherein the semipermeable membrane has a pore-size cut-off in the range of 90 kD to 140 kD.

21. The method of claim 17, wherein said bioreactor further includes a semipermeable membrane disposed intermediate the second side of the liver tissue and the second flow space.

22. The method of claim 21, wherein the semipermeable membrane has a pore-size cut-off in the range of 90 kD to 140 kD.

* * * * *